(12) United States Patent
Zapata

(10) Patent No.: US 6,793,674 B2
(45) Date of Patent: Sep. 21, 2004

(54) EYE ENDOPLANT FOR THE REATTACHMENT OF A RETINA

(75) Inventor: Ulises Zertuche Zapata, Torreon (MX)

(73) Assignee: Scieran Technologies, Inc., Laguna Hills, CA (US)

(*) Notice: Subject to any disclaimer, the term of this patent is extended or adjusted under 35 U.S.C. 154(b) by 0 days.

(21) Appl. No.: 10/686,173

(22) Filed: Oct. 14, 2003

(65) Prior Publication Data

US 2004/0097984 A1 May 20, 2004

Related U.S. Application Data

(60) Division of application No. 09/780,107, filed on Feb. 9, 2001, now Pat. No. 6,699,285, which is a continuation-in-part of application No. 09/404,744, filed on Sep. 24, 1999, now abandoned.

(51) Int. Cl.[7] .................................................. A61F 2/16
(52) U.S. Cl. ........................ 623/6.63; 606/107; 606/139
(58) Field of Search .................... 607/53, 54; 623/6.63; 606/107, 139, 213; 128/898

(56) References Cited

U.S. PATENT DOCUMENTS

| | | | | |
|---|---|---|---|---|
| 4,784,138 A | * | 11/1988 | Sinnett ....................... 606/185 |
| 5,098,443 A | * | 3/1992 | Parel et al. ................. 128/898 |
| 5,688,264 A | * | 11/1997 | Ren et al. ..................... 606/15 |
| 5,941,250 A | * | 8/1999 | Aramant et al. ............ 128/898 |
| 6,117,170 A | * | 9/2000 | Batdorf, Sr. ................. 623/4.1 |
| 6,416,522 B1 | * | 7/2002 | Strecker ...................... 606/143 |
| 2003/0028225 A1 | * | 2/2003 | Chow et al. .................. 607/54 |

* cited by examiner

Primary Examiner—Bruce E Snow
(74) Attorney, Agent, or Firm—Irell & Manella LLP

(57) ABSTRACT

A band that can be implanted into an eye to re-attach a retina. The implanted band exerts a pressure that presses the retina into a globe of the eye. The band has a length that is at least 100 degrees of the circumference of the globe of the eye. The band may be injected into the eye with a syringe type injector.

4 Claims, 2 Drawing Sheets

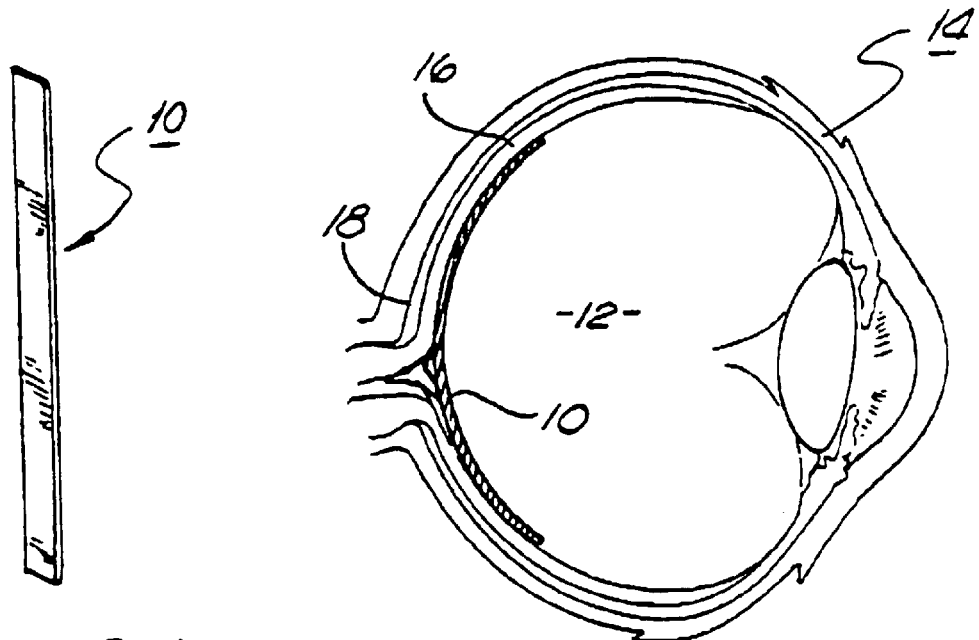
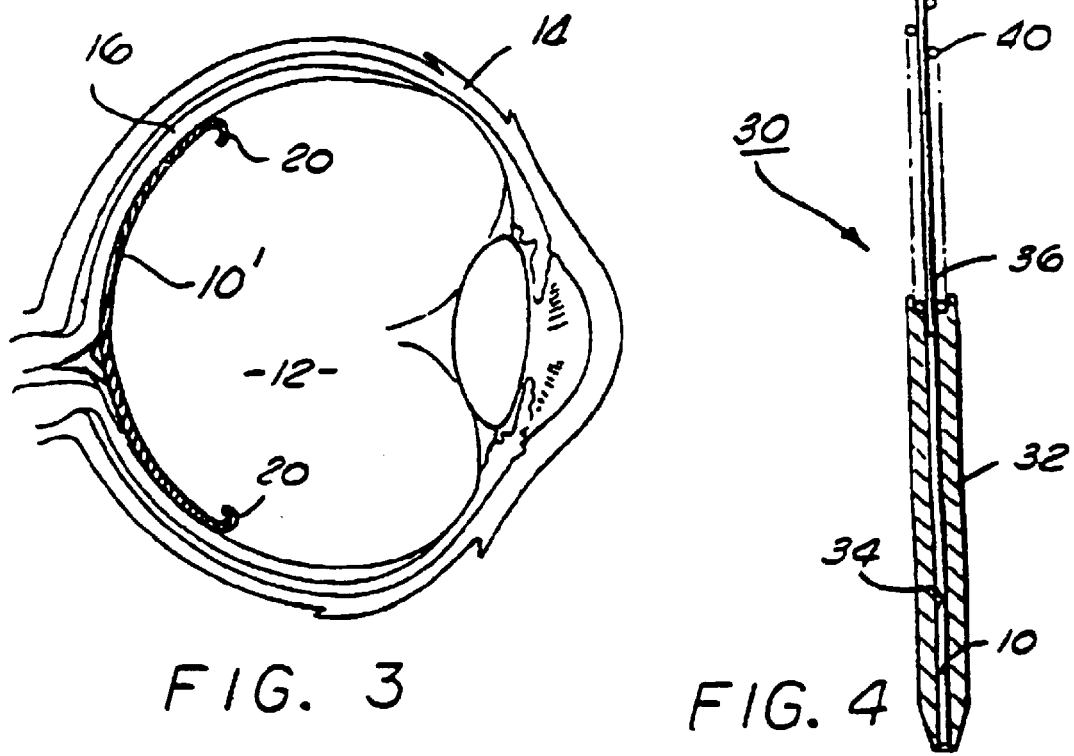

EYE ENDOPLANT FOR THE REATTACHMENT OF A RETINA

This application is a divisional of application Ser. No. 09/780,107, filed on Feb. 9, 2001, Now U.S. Pat. No. 6,699,285, which is a continuation-in-part of application No. 09/404,744, filed on Sept. 24, 1999 Now ABN.

BACKGROUND OF THE INVENTION

1. Field of the Invention

The present invention relates to a device and method for re-attaching the retina of a cornea.

2. Background Information

It has been found that the retina may become detached from the globe of a patient's eye. The detached retina may reduce the patient's field of vision. Fluid typically builds up between the detached portion of the retina and the globe to prevent a natural re-attachment.

There have been various procedures developed for re-attaching the retina. In one procedure a gas bubble is created within the eye to press the detached retina back into the globe. Unfortunately, the patient must remain face down for an extended period of time so that the force exerted by the gas does not shift away from the retina. Remaining face down can be burdensome and lead to non-compliance on the part of the patient.

There has also been other procedures developed wherein the eye is filled with a silicone oil to exert a pressure on the detached retina. Silicone oil can have a negative effect on the lens and the cornea. Additionally, the silicone oil has been known to leak behind the detached retina and prevent re-attachment. It would be desirable to provide a retina reattachment device that does not have the disadvantages of gas or silicone oil.

U.S. Pat. No. 5,527,356 issued to Peyman et al. discloses a retinal plug that is inserted into an eye to plug a hole in the retina. The plug prevents egress of vitreous fluid into the subretinal space and the migration of pigmented retinal cells. The Peyman plug does not press against the retina to induce retinal reattachment to the globe.

SUMMARY OF THE INVENTION

One embodiment of the present invention is a band that can be inserted into an eye to re-attach a retina. The inserted band exerts a pressure that presses the retina into the globe of the eye. The band has a length that is at least 100 degrees of the circumference of the globe of the eye. The band may be injected into the eye with an injector.

BRIEF DESCRIPTION OF THE DRAWINGS

FIG. 1 is a perspective view of an embodiment of a band of the present invention;

FIG. 2 is a side view of a band implanted into an eye;

FIG. 3 is a perspective view of an alternate embodiment of a band implanted into an eye;

FIG. 4 is a cross-sectional view of an injector that can inject a band into an eye;

DETAILED DESCRIPTION

Figure 5:
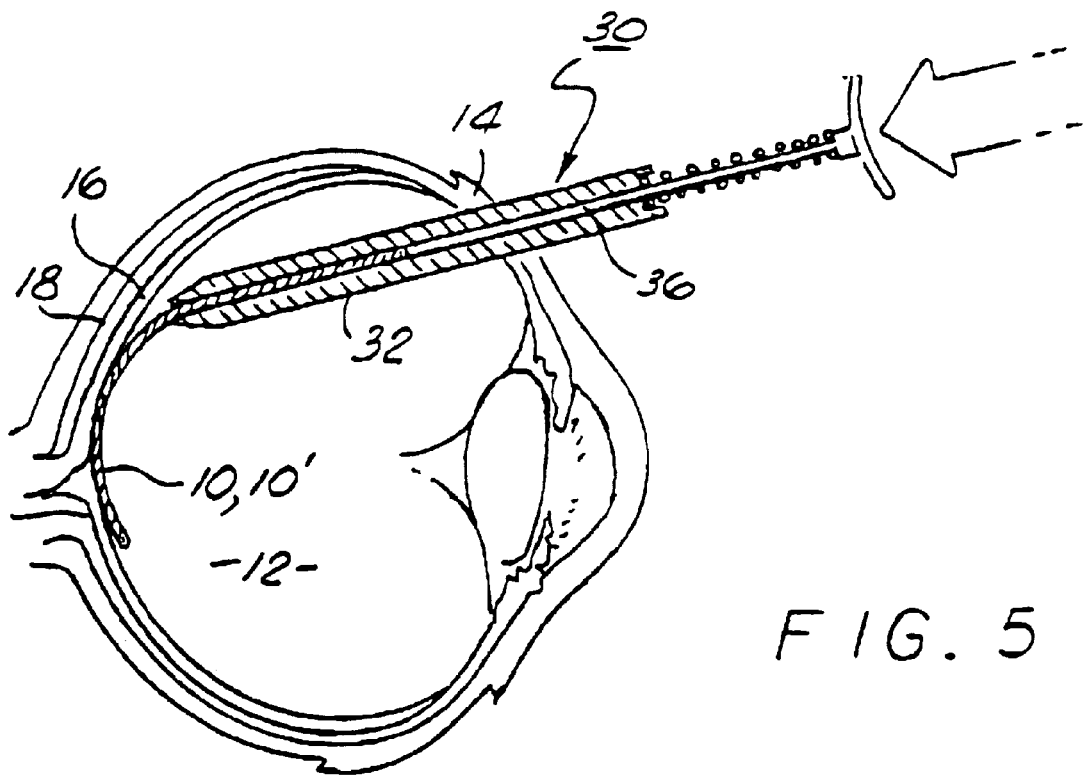
FIG. 5 is a cross-sectional view showing a band being injected into an eye.

Referring to the drawings more particularly by reference numbers, FIG. 1 shows an embodiment of a band 10 of the present invention. As shown in FIG. 2, the band 10 may be implanted into a posterior chamber 12 of an eye 14 to re-attach a retina 16 to a globe 18. The band 10 may have a naturally straight shape when in a relaxed position. When inserted into the posterior chamber 12 the band 10 may be flexible enough to conform to the radial surface of the globe 18, but stiff enough to provide a pressure onto the retina 16. The bent band 10 will create a spring force that presses the retina 16 into the globe 18. The band pressure allows the retina 16 to become re-attached to the globe 18.

The band 10 is preferably constructed from a material that is flexible enough to bend along the posterior chamber 12 and yet stiff enough to exert a pressure that will press the retina 16 into the globe 18. By way of example, the band 10 may be constructed from a silicone rubber material, or a plastic material such as an acrylic. As another embodiment, the band 10 may be a rubber-covered wire. It is desirable to provide a band length that is at least 100 degrees of the circumference of the globe 16. This may insure that the band 10 will bend to create a pressure sufficient to press the retina 16 into the globe 18. The band 10 should also be thin enough to fit within the posterior chamber 12.

FIG. 3 shows another embodiment of a band 10' that has a pair of curled ends 20. The curled ends 20 insure that the band 10' does not penetrate the retina 16 when implanted into the posterior chamber 12.

FIG. 4 shows an embodiment of an injector 30 that can be used to inject a band 10 into the posterior chamber 12. The injector 30 may include a cannula 32, which has an inner channel 34 that can receive the band 10. The cannula 32 preferably has an outer diameter that can be inserted through an incision in the eye 14. The injector 30 may include a plunger 36 that can be depressed by a surgeon to eject the band 10 from the inner channel 34 and into the posterior chamber 12. The plunger 36 may have a head portion 38, which more evenly distributes the thumb pressure of the surgeon. The injector 30 may also have a spring 40 that moves the plunger 36 back to the original position when the surgeon releases the head portion 38. Although the band 10 is shown and described, it is to be understood that the injector 30 may be adapted to eject the band 10' of FIG. 2 into the posterior chamber 12. As an alternate embodiment the band 10 may be introduced into the eye with a curved needle.

As shown in FIG. 5, the detached retina 16 can be re-attached to the globe 18 by initially injecting the band 10 or 10' into the posterior chamber 12 with the injector 30. The injector 30 may be provided in a sealed package with the band 10 already loaded into the cannula inner channel 34 so that the surgeon merely has to insert the cannula 32 through an incision in the cornea and depress the plunger 36.

The surgeon may then remove the injector 30 and insert a forcep instrument (not shown). The surgeon may use the forcep to bend the band 10 into the position shown in FIG. 2. The band 10 may be removed after a time period sufficient to allow the retina 16 to become re-attached to the globe 18. The implanted band 10 of the present invention does not require the patient to remain in a face down position. Additionally, the band 10 does not damage the cornea or lens and does not flow between the retina and globe as is found with silicone oils used in the prior art.

Figure 6:
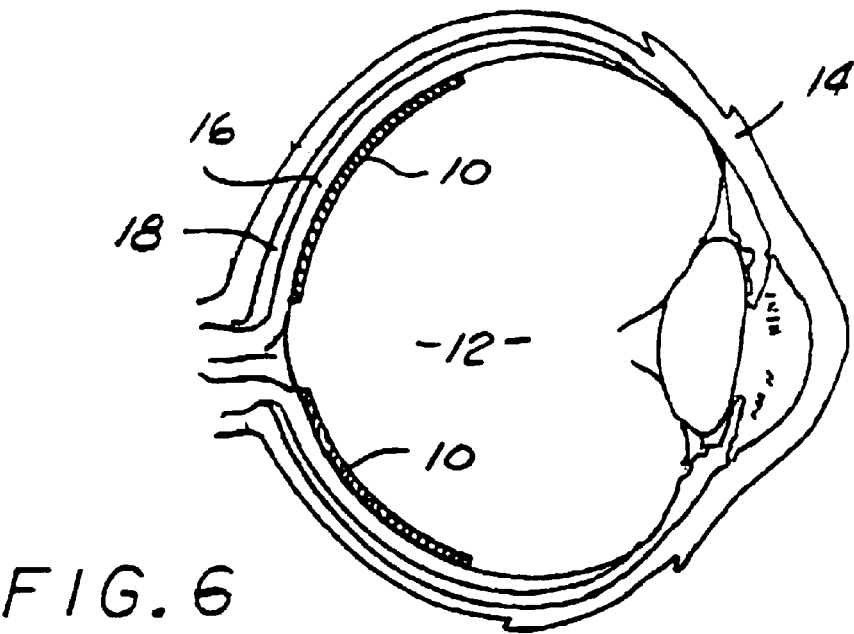
FIG. 6 is a side perspective view showing a pair of bands implanted into the eye.

FIG. 6 shows a pair of bands 10 that are implanted within the posterior chamber 12. The number of bands 10 and length of bands 10 may be varied in accordance with the location and extend of retinal detachment.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for re-attaching a retina within an eye having a globe that has a circumference, comprising:

inserting a first band into the eye; and, bending the first band against the retina such that the first band extends over at least 100 degrees of the circumference of the globe.

2. The method of claim 1, further comprising the steps of inserting a second band into the eye and bending the second band against the retina.

3. The method of claim 1, wherein the first band is inserted into the eye with an injector.

4. The method of claim 1, further comprising the step of removing the first band.

* * * * *